United States Patent [19]

Nikam

[11] Patent Number: 6,015,800
[45] Date of Patent: Jan. 18, 2000

[54] SUBSTITUTED QUINOXALINE-2-ONES AS GLUTAMATE RECEPTOR ANTAGONISTS

[75] Inventor: Sham Shridhar Nikam, Ann Arbor, Mich.

[73] Assignee: Warner-Lambert Company, Morris Plains, N.J.

[21] Appl. No.: 09/079,668

[22] Filed: May 15, 1998

Related U.S. Application Data

[60] Provisional application No. 60/057,478, Sep. 3, 1997.

[51] Int. Cl.[7] ............. A61K 31/495; C07D 241/44; C07D 403/10
[52] U.S. Cl. .............. 514/85; 514/249; 544/295; 544/337; 544/354; 544/230
[58] Field of Search ................... 544/354, 337, 544/295; 514/249, 85

[56] References Cited

U.S. PATENT DOCUMENTS

| | | | |
|---|---|---|---|
| 4,943,576 | 7/1990 | Glombik et al. | 514/249 |
| 5,283,244 | 2/1994 | Sakamoto et al. | 514/249 |
| 5,614,508 | 3/1997 | Nikam | 514/80 |
| 5,654,303 | 8/1997 | Kornberg et al. | 514/249 |

FOREIGN PATENT DOCUMENTS

| | | |
|---|---|---|
| 0708093 | 4/1996 | European Pat. Off. . |
| 4217952 | 12/1993 | Germany . |
| 3210368 | 9/1991 | Japan . |
| 9308173 | 9/1993 | WIPO . |
| 9419340 | 9/1994 | WIPO . |
| 9425469 | 11/1994 | WIPO . |
| 9426737 | 11/1994 | WIPO . |
| 9426746 | 11/1994 | WIPO . |

OTHER PUBLICATIONS

Bieeg et al, *Current Opinions in Therapeutic Patents* p. 951–989, 1993.
Klockgether et al, *Annals of Neurology* 30, p. 717–723, 1991.
Klockgether et al, *Annals of Neurology* 34, p. 585–593, 1993.
Francis et al, *Journal of Neurochemistry* 60, p. 1589–1604, 1993.
Abstract for JP 3210368 (Sep. 13, 1991).
Abstract for EP 708093 (Apr. 24, 1996).
Abstract for WWO 94/25469 (Nov. 10, 1994).
Abstract for WO 94/26737 (Nov. 24, 1994).
Abstract for Wo 93/08173 (Apr. 29, 1993).
Abstract for DE 4217952 (Dec. 2, 1993).

*Primary Examiner*—Emily Bernhardt
*Attorney, Agent, or Firm*—Elizabeth M. Anderson

[57] ABSTRACT

A novel series of substituted quinoxaline 2-ones useful as neuroprotective agents are taught. Novel intermediates, processes of preparation, and pharmaceutical compositions containing the compounds are also taught. The compounds are glutamate receptor antagonists and are useful in the treatment of stroke, cerebral ischemia, or cerebral infarction resulting from thromboembolic or hemorrhagic stroke, cerebral vasospasms, hypoglycemia, cardiac arrest, status epilepticus, perinatal asphyxia, anoxia, seizure disorders, pain, Alzheimer's, Parkinson's, and Huntington's Diseases.

4 Claims, No Drawings

SUBSTITUTED QUINOXALINE-2-ONES AS GLUTAMATE RECEPTOR ANTAGONISTS

This application claims priority of Provisional Application Ser. No. 60/057,478 filed Sep. 3, 1997.

BACKGROUND OF THE INVENTION

This invention is for novel glutamate receptor antagonists which are new compounds of the substituted quinoxaline 2-ones type. The compounds are active as excitatory amino acid receptor antagonists acting at glutamate receptors, including either or both N-methyl-D-aspartate (NMDA) receptors and non-NMDA receptors such as the α-amino-3-hydroxy-5-methyl-4-isoxazole propionic acid (AMPA) receptor and the kainate receptor. The invention also relates to the use of those quinoxaline 2-ones as neuroprotective agents for treating conditions such as cerebral ischemia or cerebral infarction resulting from a range of phenomena, such as thromboembolic or hemorrhagic stroke, cerebral vasospasms, hypoglycemia, cardiac arrest, status epilepticus, perinatal asphyxia, anoxia such as from drowning, pulmonary surgery, and cerebral trauma, as well as to treat chronic neurodegenerative disorders such as Alzheimer's Disease, Parkinsonism, and Huntington's Disease, and as anticonvulsants. The compounds of the present invention may also be useful in the treatment of schizophrenia, epilepsy, anxiety, pain, and drug addiction. Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor, the α-amino-3-hydroxy-5-methyl-4-isoxazole propionic acid (AMPA) receptor, and the kainate receptor. AMPA/kainate receptors may be referred to jointly as non-NMDA receptors. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma, as well as Alzheimer's Disease, Parkinson's Disease, and Huntington's Disease.

Several classes of quinoxalinedione derivatives have been disclosed as glutamate (EAA) receptor antagonists. For example, among excitatory amino acid receptor antagonists recognized for usefulness in the treatment of disorders are those that block AMPA receptors (Bigge C. F. and Malone T. C., *Curr. Opin. Ther. Pat.*, 1993:951; Rogawski M. A., *TiPS*, 1993;14:325). AMPA receptor antagonists have prevented neuronal injury in several models of global cerebral ischemia (Li H. and Buchan A. M., *J. Cerebr. Blood Flow Metab.*, 1993;13:933; Nellgård B. and Wieloch T., *J. Cerebr. Blood Flow Metab.*, 1992;12:2) and focal cerebral ischemia (Bullock R., Graham D. I., Swanson S., McCulloch J., *J. Cerebr. Blood Flow Metab.*, 1994;14:466; Xue D., Huang Z. -G., Barnes K., Lesiuk H. J., Smith K. E., Buchan A. M., *J. Cerebr. Blood Flow Metab.*, 1994; 14:251). AMPA antagonists have also shown efficacy in models for analgesia (Xu X. -J., Hao J. -X, Seiger A., Wiesenfeld-Hallin Z., *J. Pharmacol. Exp. Ther.*, 1993;267:140), and epilepsy (Namba T., Morimoto K., Sato K., Yamada N., Kuroda S., Brain Res., 1994;638:36; Brown S. E., McCulloch J., *Brain Res.*, 1994;641:10; Yamaguchi S. I., Donevan S. D., Rogawski M. A., *Epilepsy Res.*, 1993;15:179; Smith S. E., Durmuller N., Meldrum B. S., *Eur. J. Pharmacol.*, 1991;201:179). AMPA receptor antagonists have also demonstrated promise in chronic neurodegenerative disorders such as Parkinsonism (Klockgether T., Turski L., Honoré T., Zhang Z., Gash D. M., Kurlan R., Greenamyre J. T., *Ann. Neurol.*, 1993 ;34(4):585–593).

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain, and anxiety, and may be a significant causal factor in chronic neurodegenerative disorders such as Parkinson's disease (Klockgether T., Turski L., *Ann. Neurol.*, 1993;34:585–593), human immunodeficiency virus (HIV) related neuronal injury, amyotrophic lateral sclerosis (ALS), Alzheimer's disease (Francis P. T., Sims N. R., Procter A. W., Bowen D. M., *J. Neurochem.*, 1993;60(5):1589–1604), and Huntington's disease. (See Lipton S., *TINS*, 1993;16(12):527–532; Lipton S. A., Rosenberg P. A., *New Eng. J. Med.*, 1994;330(9):613–622; and Bigge C. F., *Biochem. Pharmacol.*, 1993;45:1547–1561 and references cited therein.) NMDA receptor antagonists may also be used to prevent tolerance to opiate analgesia or to help control withdrawal symptoms from addictive drugs (Eur. Pat. Appl. 488,959A).

The compounds of the instant invention differ from the art in that they provide compounds which have one amide functionality in the quinoxaline mix and a variety of substituents at C-3 position. These structural features provide compounds with greater aqueous solubility and, with the appropriate substitutions have better CNS penetration. These are important attributes in pharmaceuticals.

An object of this invention is to provide novel quinoxaline 2-ones which function as antagonists.

SUMMARY OF THE INVENTION

The present invention is a compound of Formula I:

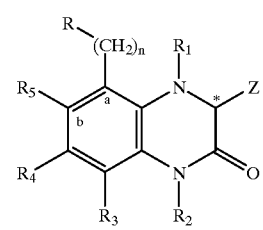

I or a pharmaceutically acceptable salt thereof wherein R, $R_1$, $R_2$, $R_3$, $R_4$, $R_5$, Z, *, and n are as described below.

The instant invention is also related to a pharmaceutical composition containing the compound defined by Formula I in an amount effective to treat cerebrovascular disorders responsive to the blockade of glutamate receptors (such as the α-amino-3-hydroxy-5-methyl-4-isoxazole propionic acid (AMPA) receptor and the kainate receptor), and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's disease, ALS, Parkinsonism, and Alzheimer's disease. The pharmaceutical composition of this invention may also be employed as an analgesic or the treatment of epilepsy.

The invention further relates to a method of treating cerebrovascular disorders responsive to antagonism of glutamate receptors NMDA by administering a compound of above-defined Formula I in a unit dosage form.

Another object of this invention is to provide a method of treating disorders responsive to the antagonism of glutamate or aspartate receptors in a human by administering a pharmaceutically effective amount of the quinoxaline 2-ones of this invention.

Another object of this invention is to provide novel methods of preparing the quinoxaline 2-ones.

A further object of this invention is directed to novel intermediates useful in the preparation of the quinoxaline 2-ones of this invention.

DETAILED DESCRIPTION OF THE INVENTION

The substituted quinoxaline 2-ones of the instant invention are those of Formula I

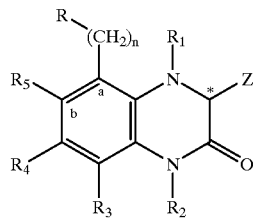

I or a pharmaceutically acceptable salt thereof wherein
* indicates R, S, or RS(±);
R is an amino acid derivative,
secondary or tertiary amine,
cyclic amine,
amide,
carbamate,
urea or thiourea, or
sulfonamide;
n is an integer of from 1 to 4;
$R_1$ is hydrogen,
alkyl,
aralkyl,
carboxyalkyl,
phosphoroalkyl, or
phosphonoalkyl;
$R_2$ is hydrogen,
hydroxy, or
amino;
$R_3$ and $R_4$ are each independently
hydrogen,
alkyl,
alkenyl,
cycloalkyl,
halogen,
haloalkyl,
nitro,
cyano,
$SO_2CF_3$,
$C(O)R_6$,
C(O)OH,
$(CH_2)_mSO_3H$,
$(CH_2)_mSO_2R_6$,
$(CH_2)_mCO_2R_9$ wherein $R_9$ is hydrogen, alkyl, aralkyl, or cycloalkyl,
$(CH_2)_mCONR_7R_8$,
$(CH_2)_mSO_2NR_7R_8$, or
$NHCOR_6$ wherein m is an integer of from 0 to 4, $R_6$ is alkoxy,

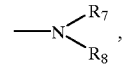

alkyl, haloalkyl, aryl, or aralkyl, and $R_7$ and $R_8$ are each independently hydrogen, alkyl, cycloalkyl, aralkyl, or aryl;
$R_5$ is hydrogen,
alkyl,
alkenyl,
alkynyl,
cycloalkyl,
halogen,
haloalkyl,
aryl,
aralkyl,
heteroaryl,
nitro,
cyano,
$SO_2CF_3$,
$C(O)R_6$,
COOH,
$(CH_2)_mCO_2R_9$,
$(CH_2)_mCONR_7R_8$,
$(CH_2)_mSO_3H$,
$(CH_2)_mSO_2R_6$,
$(CH_2)_mSO_2NR_7R_8$, or
$NHCOR_6$ wherein m, $R_7$, and $R_8$ are as defined above;
$R_5$ and the $R(CH_2)_n$— side chain may be at the a or b position on the ring; and Z is the side-chain of an α-amino acid or hydrogen.

The compounds of Formula I are capable of forming pharmaceutically acceptable acid addition salts.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as a mixture of cis and trans isomers or R- and S-isomers, or as the individual cis and trans isomers or R- and S-isomers. The mixture of isomers as well as the individual isomers are intended to be encompassed within the scope of the present invention.

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "carboxyalkyl" means alkyl as above and attached to a carboxy group.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

The term "alkynyl" means a straight or branched chain alkynyl group of 2 to 6 carbon atoms, for example, but not limited to ethynyl, 2,3-propynyl, 2,3- or 3,4-butylnyl.

"Alkoxy" is O-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "aralkyl" means aryl and alkyl as defined above and includes but is not limited to benzyl, 2-phenylethyl, 3-phenylpropyl; a preferred group is benzyl.

The term "heteroaryl" means a heteroaromatic radical which is 2-, 3-, or 4-pyridinyl, 2-, 4-, or 5-pyrimidinyl, or 2-, or 3-thienyl.

"Halogen" is fluorine, chlorine, bromine, or iodine.

The term "haloalkyl" is halogen and alkyl as defined above such as, but not limited to, trifluoromethyl and trichloromethyl.

AMINO ACID DERIVATIVES

R is an amino acid derivative of formula

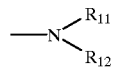

wherein $R_{11}$ is hydrogen, alkyl, or aralkyl, and $R_{12}$ is an amino acid of formula

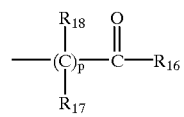

wherein p is an integer of from 1 to 5 and $R_{17}$ and $R_{18}$ are each independently on any carbon in —$(C)_p$— and wherein $R_{16}$ is hydroxy, alkoxy, $NR_{19}R_{20}$ wherein $R_{19}$ and $R_{20}$ are each independently hydrogen, alkyl, cycloalkyl, or aralkyl, and $R_{17}$ and $R_{18}$ are independently selected from hydrogen, alkyl, cycloalkyl, heterocycloalkyl, aryl, aralkyl, heteroaralkyl, carboxyalkyl, aminoalkyl, thioalkyl, or hydroxyalkyl.

Amino acid derivatives are common amino acids, the naturally occurring α-amino acids, unnatural amino acids, substituted β, γ, δ amino acids and their enantiomers.

Common amino acids are: Alanine, β-alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Modified and unusual amino acids are as would occur to a skilled chemist and are, for example, but not limited to:

10,11-Dihydro-5H-dibenzo[a,d]cyclohepten-5-yl)glycine or -Amino-10,11-dihydro-5H-dibenzo[a,d] cycloheptene-5-acetic acid (Paraphenyl)phenylalanine, 3,3-Diphenylalanine, 3-Hydroxyproline, 4-Hydroxyproline, N-Methylphenylalanine, N-Methylaspartic acid, N-Methylisoleucine, N-Methylvaline, Norvaline, Norleucine, Ornithine, 2-Aminobutyric acid, 2-Amino-4-pentanoic acid (Allylglycine), $N^G$-nitroarginine, 2-Amino-3-(2-amino-5-thiazole)propanoic acid, 2-Amino-3-cyclopropanepropanoic acid (Cyclopropylalanine), Cyclohexylalanine (Hexahydrophenylalanine), N-Methylcyclohexylalanine (N-Methylhexahydrophenylalanine), 2-Amino-4,4(RS)-epoxy-4-pentanoic acid, $N^{im}$-2,4-Dinitrophenylhistidine, 2-Aminoadipic acid,
2-Amino-5-phenylpentanoic acid (Homophenylalanine),
Methionine sulfoxide,
Methionine sulfone,
3-(1'-Naphthyl)alanine,
3-(2'-Naphthyl)alanine,
2-Amino-3-cyanopropanoic acid (Cyanoalanine),
Phenylglycine,
2-Aminopentanoic acid (Prolylglycine),
2-Amino-6-(1-pyrrolo)-hexanoic acid,
2-Amino-3-(3-pyridyl)-propanoic acid (3-Pyridylalanine),
1,2,3,4-Tetrahydro-3-isoquinolinecarboxylic acid,
2-Amino-3-(4-thiazolyl)-propanoic acid,
O-tertiary butyl-tyrosine,
O-Methyl-tyrosine,
O-Ethyl-tyrosine,
$N^{in}$-Formyl-tryptophan,
5H-Dibenzo[a,d]cycloheptene glycine,
9H-Thioxanthene glycine, and
9H-Xanthene glycine.
Preferred amino acid derivatives are:

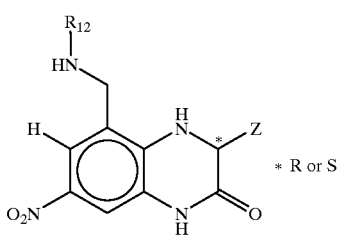

\* R or S

1. $R_{12}$ is —$CH_2CO_2H$, Z is H
2. $R_{12}$ is —$CH_2CO_2H$, Z is $CH_3$
3. $R_{12}$ is —$CH_2CO_2H$,

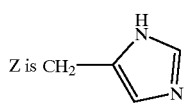

Z is $CH_2$—

4. $R_{12}$ is —$CH_2CO_2H$, Z is $CH_2CO_2H$
5. $R_{12}$ is —$CH_2CH_2CO_2H$, Z is H
6. $R_{12}$ is —$CH_2CH_2CH_2CO_2H$, Z is H
7. $R_{12}$ is —$CH_2CH_2CH_2CO_2H$, Z is $CH_2CO_2H$

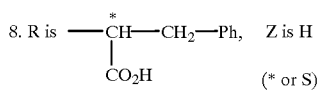

8. R is —CH—$CH_2$—Ph, Z is H, $CO_2H$ (\* or S)

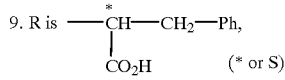

9. R is —CH—$CH_2$—Ph, $CO_2H$ (\* or S)

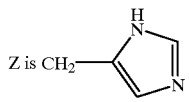

Z is $CH_2$—

1. [(7-Nitro-2-oxo-1,2,3,4-tetrahydro-quinoxalin-5-ylmethyl)-amino]-acetic acid

2. [(3-Methyl-7-nitro-2-oxo-1,2,3,4-tetrahydro-quinoxalin-5-ylmethyl)-amino]-acetic acid
3. {[3-(3H-Imidazol-4-ylmethyl)-7-nitro-2-oxo-1,2,3,4-tetrahydro-quinoxalin-5-ylmethyl]-amino}-acetic acid
4. [(3-Carboxymethyl-7-nitro-2-oxo-1,2,3,4-tetrahydro-quinoxalin-5-ylmethyl)-amino]-acetic acid
5. 3-[(7-Nitro-2-oxo-1,2,3,4-tetrahydro-quinoxalin-5-ylmethyl)-amino]-propionic acid
6. 4-[(7-Nitro-2-oxo-1,2,3,4-tetrahydro-quinoxalin-5-ylmethyl)-amino]-butyric acid
7. 4-[(3-Carboxymethyl-7-nitro-2-oxo-1,2,3,4-tetrahydro-quinoxalin-5-ylmethyl)-amino]-butyric acid
8. (S)-[2-[(7-Nitro-2-oxo-1,2,3,4-tetrahydro-quinoxalin-5-ylmethyl)-amino]-3-phenyl-propionic acid
9. [S-(R\*,R\*)]OR[S-(R\*,S\*)]-2-{[3-(3H-Imidazol-4-ylmethyl)-7-nitro-2-oxo-1,2,3,4-tetrahydro-quinoxalin-5-ylmethyl]-amino}-3-phenyl-propionic acid

SECONDARY OR TERTIARY AMINES (ALKYL AMINES)

R is a secondary or tertiary amine,

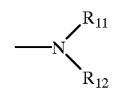

and
may be at the a-position and

may be at the b-position on the ring;
n is an integer of from 1 to 4,
$R_{11}$ and $R_{12}$ are each independently
hydrogen,
alkyl,
alkenyl,
alkynyl,
cycloalkyl,
heterocycloalkyl,

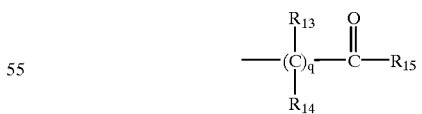

wherein q is an integer of from 0 to 3 and $R_{13}$ and $R_{14}$ are each independently selected from hydrogen, alkyl, aralkyl, cycloalkyl, and heteroalkyl and $R_{15}$ is alkyl, aryl, aralkyl, heteroaralkyl, heteroaryl and $NR_{16}R_{17}$ wherein $R_{16}$ and $R_{17}$ are each independently selected from hydrogen, alkyl, and aryl,
hydroxyalkyl,
aminoalkyl, alkylaminoalkyl,
thioalkyl,

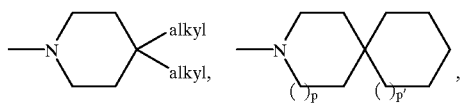

wherein p and p' are each independently an integer selected from 0 and 1 and wherein in the second ring 1 or 2 carbon atoms can be replaced by 1 or 2 heteroatoms selected from N, O, or S.

In

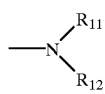

the $R_{11}$ and $R_{12}$ are not joined and are not amino acids. The group is a secondary or tertiary amine bearing substituted alkyl groups. These include hydrogen, alkyl, for example, the group can be

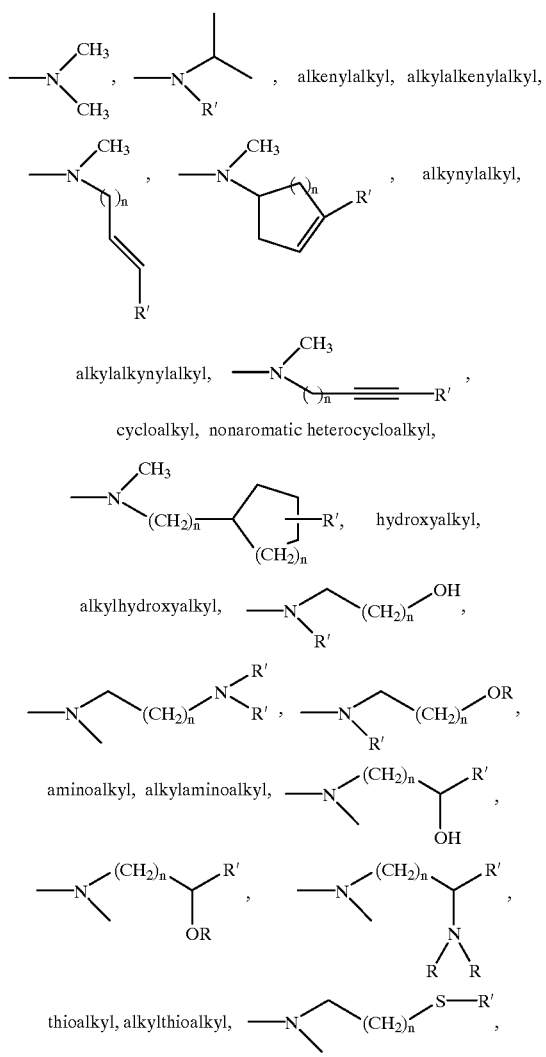

-continued

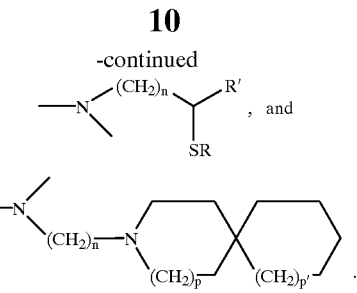

Preferred compounds are those of Formula I wherein

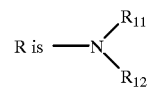

wherein $R_{11}$ and $R_{12}$ are each independently
hydrogen,
alkyl,
cycloalkyl,
nonaromatic heterocycloalkyl,
$R_{13}$ and $R_{14}$=independently hydrogen, alkyl, aralkyl, cycloalkyl,
heteroaralkyl,

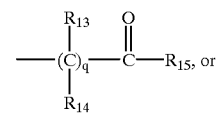

wherein q is an integer of from 0 to 3 and $R_{15}$ is
alkyl,
aralkyl,
aryl,
heteroaryl,
$NR_{16}R_{17}$ wherein $R_{16}$ and $R_{17}$ are each independently selected from
hydrogen,
alkyl, and
aryl.

More preferred compounds are those of Formula I wherein $R_{11}$ and $R_{12}$ are each independently
hydrogen,
methyl,
ethyl,
propyl,
butyl,
cycloalkyl,
heterocycloalkyl,
alkylaminoalkyl,
aminoalkyl,
hydroxyalkyl, and
alkoxyalkyl.

Still more preferred compounds are those of Formula I wherein $R_{11}$ and $R_{12}$ are each independently
hydrogen,
methyl,
ethyl,
propyl, butyl, or cyclohexyl.

Alkylamines include compounds such as

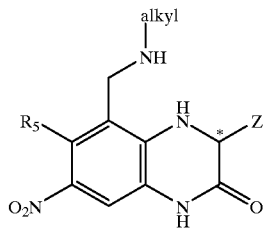

wherein * is R, S, or RS(±);

Z is —CH$_3$, —CH$_2$OH, —CH$_2$CO$_2$H, —CH$_2$SH, or;

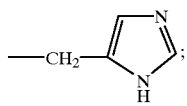

R$_5$ is hydrogen or chloro; and alkyl is methyl, ethyl, propyl, isopropyl, and the like.

Primary amines are as above for alkyl amines except the substituent is —NH$_2$ instead of the NH(alkyl).

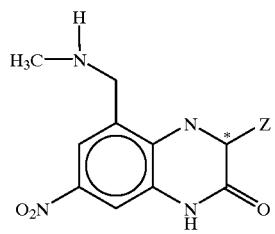

1. Z is H
2. Z is CH$_2$OH

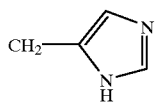

4. Z is CH$_2$CO$_2$H
5. Z is CO$_2$H 1. 5-Methylaminomethyl-7-nitro-3,4-dihydro-1H-quinoxalin-2-one
2. 3-Hydroxymethyl-5-methylaminomethyl-7-nitro-3,4-dihydro-1H-quinoxalin-2-one
3. 3-(3H-Imidazol-4-ylmethyl)-5-methylaminomethyl-7-nitro-3,4-dihydro-1H-quinoxalin-2-one
4. (8-Methylaminomethyl-6-nitro-3-oxo-1,2,3,4-tetrahydro-quinoxalin-2-yl)-acetic acid
5. 8-Methylaminomethyl-6-nitro-3-oxo-1,2,3,4-tetrahydro-quinoxaline-2-carboxylic acid Tertiary amines are as above for alkyl amines except the substituent is

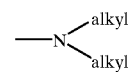

wherein alkyl is CH$_3$, C$_2$H$_5$, C$_3$H$_7$, and the like as would occur to a skilled artisan.

CYCLIC AMINES

Cyclic amines are compounds of Formula I wherein

R is a mono- or bicyclic ring unsubstituted or substituted by from 1 to 4 substituents, R is attached to the quinoxaline ring through N(—CH$_2$)$_n$ and at the a- or b-position and R is

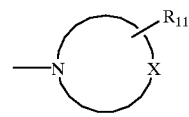

of from 4 to 7 atoms or

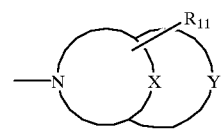

of from 8 to 12 atoms wherein R$_{11}$ is from 1 to 4 substituents independently selected from hydrogen, hydroxy, hydroxyalkyl, alkyl, alkoxy, alkoxyalkyl,

—NR$_{13}$R$_{14}$, aminoalkyl, alkenyl, alkynyl, thiol, thioalkyl, alkylthioalkyl, aryl, aralkyl, heteroaryl, heteroaralkyl, cycloalkyl,

—SO$_2$R$_{15}$,

—SO$_2$NR$_{13}$R$_{14}$,

—(CH$_2$)$_n$SO$_2$NR$_{13}$R$_{14}$, and

—(CH$_2$)$_n$SO$_2$R$_{15}$;

wherein R$_{13}$ and R$_{14}$ are independently selected from hydrogen, alkyl, cycloalkyl, heterocycloalkyl, aralkyl, and aryl;
R$_{15}$ is hydroxy, alkoxy, —NR$_{13}$R$_{14}$, or haloalkyl;
R$_{11}$ may be 2 substituents attached at the same carbon;
X and Y are each independently
  carbon which is substituted by hydrogen, halogen, haloalkyl, alkyl, alkoxy, alkoxyalkyl, NR$_{13}$R$_{14}$, aminoalkyl, aralkyl, aryl, heteroaryl, heteroaralkyl, cycloalkyl, heterocycloalkyl, hydroxy, and hydroxyalkyl,
  —O—,
  —S—,
  —SO—,
  —SO$_2$—,
  —NR$_{16}$—,
wherein R$_{16}$ is alkyl, hydrogen, aralkyl, heteroaralkyl, aryl, heteroaryl, cycloalkyl,
  heterocycloalkyl, —C(O)OR$_{17}$, —C(O)R$_{17}$, —SO$_2$R$_{18}$, —SO$_2$NR$_{19}$R$_{20}$,
  —CH$_2$SO$_2$R$_{18}$, —CH$_2$SO$_2$NR$_{19}$R$_{20}$,
wherein R$_{17}$ is alkyl, aralkyl, cycloalkyl, heterocycloalkyl, aryl, or heteroaryl;
R$_{18}$ is alkyl, aralkyl, hydroxyl, or alkoxy;
R$_{19}$ and R$_{20}$ are each independently hydrogen and alkyl.

Bicyclic structures encompassed in this invention include spiro ring structures, wherein both ends of a second ring are attached to the same carbon unit on the parent ring.

For monocyclic and bicyclic structures wherein X or Y represent a carbon atom, the structure may also include an integral double bond.

More preferred are those of Formula I wherein R is

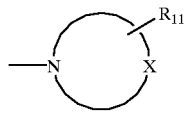

of from 4 to 7 atoms where
X is
  carbon substituted by hydrogen, haloalkyl, alkyl, alkoxy, alkoxyalkyl, NR$_{13}$R$_{14}$, aminoalkyl, cycloalkyl, heterocycloalkyl, hydroxy, and hydroxyalkyl,
  —O—,
  —NR$_{16}$—, and
  —C(O)—;
R$_{11}$ is absent,
  hydrogen,
  alkyl,
  alkoxy,
  alkoxyalkyl,
  NR$_{13}$R$_{14}$,
  aminoalkyl,
  aralkyl,
  aryl,
  heteroaryl,
  heteroaralkyl,
  cycloalkyl,
  heterocycloalkyl,
  hydroxy, or
  hydroxyalkyl,
R$_{11}$ may also represent two independent alkyl substituents to form a gem-dialkyl arrangement,
where X represents carbon, an integral double bond may be located between the C$_3$ and C$_4$ carbons of 5- to 7-membered rings.

Still more preferred are those of Formula I wherein R is

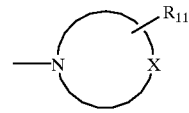

of from 4 to 7 atoms where
X is
  carbon substituted by hydrogen, alkyl, NR$_{13}$R$_{14}$, aminoalkyl, cycloalkyl, and heterocycloalkyl,
  —O—,
  —NR$_{16}$—, and
  —C(O)—;
R$_{11}$ is absent,
  hydrogen,
  hydroxy,
  hydroxyalkyl,
  alkyl,
  alkoxy,
  alkoxyalkyl,
  —NR$_{13}$R$_{14}$,
  aminoalkyl,
  cycloalkyl, or
  heterocycloalkyl;
R$_{11}$ may also represent two independent alkyl substituents to form a gem-dialkyl arrangement,
where X represents carbon, an integral double bond may be located between the C$_3$ and C$_4$ carbons of 5- to 7-membered rings.

Other preferred compounds of the invention are those of Formula I wherein R is

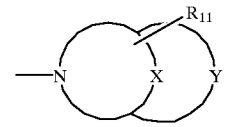

of from 8 to 12 atoms;
X and Y are each independently as described above;
R$_{11}$ is absent,
  hydrogen,
  alkyl,
  alkoxy,
  alkoxyalkyl,
  NR$_{13}$R$_{14}$,
  aminoalkyl,
  aralkyl,
  aryl,
  heteroaryl,
  heteroaralkyl,
  cycloalkyl,
  heterocycloalkyl,
  hydroxy, and
  hydroxyalkyl.

Cyclic amines include compounds such as

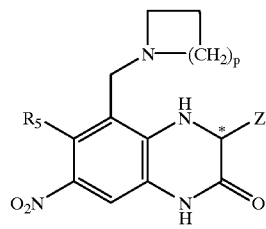

wherein * is R, S, or RS(±);
p is an integer of from 1 to 4;
Z is —CH$_3$, —CH$_2$OH, —CH$_2$CO$_2$H, —CH$_2$SH, or

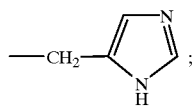

and
R$_5$ is hydrogen or chloro.
Especially preferred compounds are:

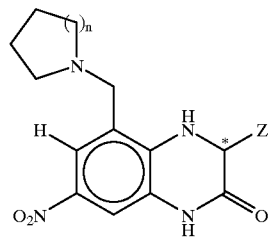

*R or S 1. n is 1, Z is H
2. n is 2, Z is H
3. n is 1, Z is CH$_2$OH
4. n is 2, Z is CH$_2$OH
5. n is , Z is

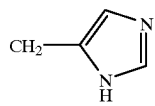

6. n is 2, Z is

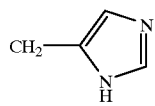

7. n is 2, Z is CH$_2$CO$_2$H
8. n is 2, Z is CH$_2$CO$_2$H
9. n is 1, Z is CO$_2$H
10. n is 2; Z is CO$_2$H
1. 7-Nitro-5-pyrrolidin-1-ylmethyl-3,4-dihydro-1H-quinoxalin-2-one
2. 7-Nitro-5-piperidin-1-ylmethyl-3,4-dihydro-1H-quinoxalin-2-one
3. 3-Hydroxymethyl-7-nitro-5-pyrrolidin-1-ylmethyl-3,4-dihydro-1H-quinoxalin-2-one
4. 3-Hydroxymethyl-7-nitro-5-piperidin-1-ylmethyl-3,4-dihydro-1H-quinoxalin-2-one
5. 3-(3H-Imidazol-4-ylmethyl)-7-nitro-5-pyrrolidin-1-ylmethyl-3,4-dihydro-1H-quinoxalin-2-one
6. 3-(3H-Imidazol-4-ylmethyl)-7-nitro-5-piperidin-1-ylmethyl-3,4-dihydro-1H-quinoxalin-2-one
7. (6-Nitro-3-oxo-8-pyrrolidin-1-ylmethyl-1,2,3,4-tetrahydro-quinoxalin-2-yl)-acetic acid
8. (6-Nitro-3-oxo-8-piperidin-1-ylmethyl-1,2,3,4-tetrahydro-quinoxalin-2-yl)-acetic acid
9. 6-Nitro-3-oxo-8-pyrrolidin-1-ylmethyl-1,2,3,4-tetrahydro-quinoxaline-2-carboxylic acid
10. 6-Nitro-3-oxo-8-piperidin-1-ylmethyl-1,2,3,4-tetrahydro-quinoxaline-2-carboxylic acid

AMIDE DERIVATIVES

Amide derivatives are compounds of Formula I wherein R is a straight chain amide

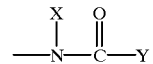

or an amide in a mono- or bicyclic ring, unsubstituted or substituted by from 1 to 4 substituents, and is

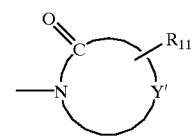

of from 4 to 7 atoms or

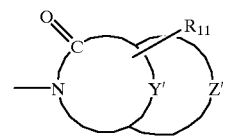

of from 8 to 12 atoms
attached at N to the quinoxaline ring through —(CH$_2$)$_n$— at the a- or b-position,
wherein
R$_{11}$ is from 1 to 4 substituents independently selected from hydrogen, hydroxy, hydroxyalkyl, alkyl, alkoxy, alkoxyalkyl, —NR$_{13}$R$_{14}$, aminoalkyl, alkenyl, alkynyl, thiol, thioalkyl, alkylthioalkyl, aryl, aralkyl, heteroaryl, heteroaralkyl, heterocycloalkyl, cycloalkyl, —SO$_2$R$_{15}$, —SO$_2$NR$_{13}$R$_{14}$, —(CH$_2$)$_n$SO$_2$NR$_{13}$R$_{14}$, and —(CH$_2$)$_n$SO$_2$R$_{15}$; wherein R$_{13}$ and R$_{14}$ are independently selected from hydrogen, alkyl, cycloalkyl, heterocycloalkyl, aralkyl, and aryl; R$_{15}$ is hydroxy, alkoxy, —NR$_{13}$R$_{14}$, or haloalkyl; or R$_{11}$ may be 2 substituents attached at the same carbon;
X is hydrogen, alkyl, aralkyl, aryl, heteroaryl, cycloalkyl, heterocycloalkyl, alkenylalkyl, alkylalkenylalkyl, alkynylalkyl, alkylhydroxyalkyl, alkylaminoalkyl;
Y is alkyl, haloalkyl, alkenylalkyl, alkylalkenylalkyl, alkynylalkyl, alkylalkynylalkyl, cycloalkyl, heterocycloalkyl, alkoxy, alkoxyalkyl, thioalkyl, alkylthioalkyl;
or is alkylaminoalkyl orarylaminoalkyl such as —(CH)$_p$(R$_{16}$)NR$_{17}$R$_{18}$, wherein p is an integer of from 1 to 6, R$_{16}$ is hydrogen, alkyl, aryl, aralkyl, and $R_{17}$ and $R_{18}$ are each independently hydrogen, alkyl, aralkyl, aryl, heteroaryl or joined together to form a saturated ring of from 4 to 7 members;

or is a natural or unnatural amino acid (α-, β-, or γ-) backbone such as $—(C^*H)_q(R_{19})NR_{20}R_{21}$ wherein the C* stereochemistry is R or S or RS. q is an integer of from 1 to 3, $R_{19}$ is hydrogen or a side chain of a natural or unnatural amino acid, $R_{20}$ and $R_{21}$ are independently hydrogen, alkyl, aralkyl, alkoxycarbonyl, and aralkoxycarbonyl;

or is carboxyalkyl or alkylcarboxyalkyl such as $—(CH)_p(R_{22})CO_2R_{23}$ wherein p is an integer of from 1 to 6, $R_{22}$ is hydrogen, alkyl, aryl, aralkyl, $R_{23}$ is hydrogen, alkyl, aralkyl, aryl, heteroaryl;

or is a side-chain amide such as $—(CH)_p(R_{24})C(O)NR_{25}R_{26}$ wherein p is an integer of from 1 to 6, $R_{24}$ is hydrogen, alkyl, aralkyl, aryl, and $R_{25}$ and $R_{26}$ are each independently hydrogen, alkyl, aralkyl, aryl, heteroaryl or joined together to form a saturated ring of from 5 to 7 members;

or is alkylheterocycloalkyl or alkylheteroaralkyl such as $—(CH_2)_q—R_{27}$ wherein q is an integer from 1 to 3 and $R_{27}$ is a heterocycle such as oxazolyl, oxadiazolyl, thiazolyl, 1,3,4-oxadiazolyl, 1,2,4-triazolyl, 1,3,4-thiadiazolyl, pyrazolyl, imidazolyl, tetrazolyl, 1,3-oxazolyl, isoxazolyl, 1,2,3-triazolyl, 1,3,4-thiazolyl.

Y' and Z' are each independently carbon which is substituted by hydrogen, halogen, haloalkyl, alkyl, alkoxy, alkoxyalkyl, $NR_{13}R_{14}$, aminoalkyl, aralkyl, aryl, heteroaryl, heteroaralkyl, cycloalkyl, heterocycloalkyl, hydroxy, and hydroxyalkyl, —O—, —S—, —SO—, —SO$_2$—, —NR$_{28}$—, wherein $R_{28}$ is alkyl, hydrogen, aralkyl, heteroaralkyl, aryl, heteroaryl, cycloalkyl, heterocycloalkyl, -C(O)OR$_{29}$, —C(O)R$_{29}$, —SO$_2$R$_{30}$, —SO$_2$NR$_{31}$R$_{32}$, —CH$_2$SO$_2$R$_{30}$, —CH$_2$SO$_2$NR$_{31}$R$_{32}$, wherein $R_{29}$ is alkyl, aralkyl, cycloalkyl, heterocycloalkyl, aryl, or heteroaryl; $R_{30}$ is alkyl, aralkyl, hydroxyl, or alkoxy; and $R_{31}$ and $R_{32}$ are each independently hydrogen and alkyl.

Bicyclic structures encompassed in this invention include spiro ring structures, wherein both ends of a second ring are attached to the same carbon unit on the parent ring.

For monocyclic and bicyclic structures wherein X or Y represent a carbon atom, the structure may also include an integral double bond.

More preferred compounds of Formula I wherein R is an amide

are those wherein
X is selected from hydrogen, alkyl, aralkyl, aryl, heteroaryl, cycloalkyl, heterocycloalkyl, and
Y is selected from alkyl, haloalkyl, cycloalkyl, heterocycloalkyl, alkynyl, alkenyl, aryl, heteroaryl, alkoxy, alkoxyalkyl, alkylaminoalkyl, carboxyalkyl;

or is a side-chain amide such as $—(CH)_p(R_{24})C(O)NR_{25}R_{26}$ wherein p is an integer of from 1 to 6, $R_{24}$ is hydrogen, alkyl, aralkyl, aryl, and $R_{25}$ and $R_{26}$ are each independently hydrogen, alkyl, aralkyl, aryl, heteroaryl, alkoxycarbonyl, aralkoxycarbonyl or joined together to form a saturated ring of from 5 to 7 members;

or is a heteroalkyl such as $—(CH_2)_q—R_{27}$ wherein q is an integer from 1 to 3 and $R_{27}$ is oxadiazolyl, thiazolyl.

Still more preferred are those of Formula I wherein R is an amide

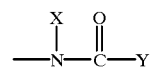

wherein
X is selected from methyl, ethyl, isopropyl, and butyl and
Y is selected from methyl, ethyl, isopropyl, propyl, butyl, benzyl, allyl, propargyl, cyclopentyl, cyclohexyl, 2- or 3-pyrrolidinyl, 2- or 3-tetrahydrofuranyl, 2-, 3-, or 4-piperidinyl, substituted phenyl, 2- or 3-furanyl, 2- or 3-thienyl, 2- or 3-benzfuranyl, 2- or 3-benzthienyl, 2- or 3-indolyl, 2-benzimidazolyl, imidazolyl, 3- or 4-piperidinyl, phenyl, 2- or 3-indolyl, tetrazolyl, imidazolyl, pyrrazolyl, naphthyl, oxadiazolyl, and 2-benzimidazolyl.

More preferred compounds of Formula I wherein R is an amide in a mono- or bi-cyclic ring, unsubstituted or substituted by from 1 to 4 substituents, and is

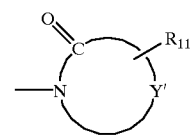

of from 4 to 7 atoms or

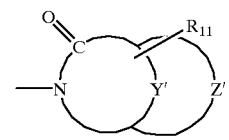

of from 8 to 12 atoms
are those wherein R is a mono-cyclic ring of from 4 to 7 atoms and Y' is methylene, O, S, or N—R$_{28}$ wherein R$_{28}$ is H, alkyl, aryl.

The open chain amides are preferred over the mono- and bicyclic amides.

Still more preferred are amide of formula:

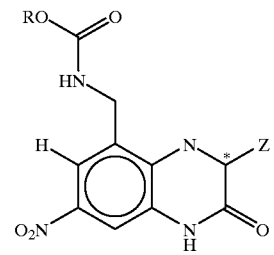

1. R is CH$_3$, Z is H
2. R is CH$_3$, Z is CO$_2$H
3. R is CH$_3$, Z is CH$_2$CO$_2$H
4. R is Ph, Z is H
5. R is Ph, Z is CH$_2$CO$_2$H
6. R is Ph, Z is CO$_2$H
7. R is Ph, Z is CH$_2$OH
1. N-(3-Hydroxymethyl-7-nitro-2-oxo-1,2,3,4-tetrahydro-quinoxalin-5-ylmethyl)-acetamide
2. [8-(Acetylamino-methyl)-6-nitro-3-oxo-1,2,3,4-tetrahydro-quinoxalin-2-yl]-acetic acid 3. 8-(Acetylamino-methyl)-6-nitro-3-oxo-1,2,3,4-tetrahydro-quinoxaline-2-carboxylic acid
4. N-(7-Nitro-2-oxo-1,2,3,4-tetrahydro-quinoxalin-5-ylmethyl)-benzamide
5. [8-(Benzoylamino-methyl)-6-nitro-3-oxo-1,2,3,4-tetrahydro-quinoxalin-2-yl]-acetic acid
6. 8-(Benzoylamino-methyl)-6-nitro-3-oxo-1,2,3,4-tetrahydro-quinoxaline-2-carboxylic acid
7. N-(3-Hydroxymethyl-7-nitro-2-oxo-1,2,3,4-tetrahydro-quinoxalin-5-ylmethyl)-benzamide

CARBAMATE DERIVATIVES

Carbamate derivatives are compounds of Formula I wherein R is a carbamate

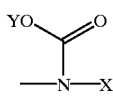

wherein X is selected from hydrogen, alkyl, aralkyl, aryl, heteroaryl, cycloalkyl, heterocycloalkyl, and Y is selected from alkyl, cycloalkyl, heterocycloalkyl, aralkyl, heteroaralkyl, aryl, heteroaryl.
More preferred are carbamate of formula

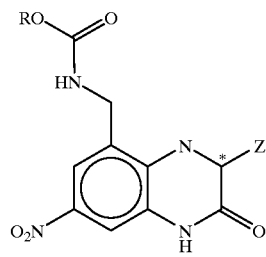

1. R is $CH_3$, Z is H
2. R is $CH_3$, Z is $CO_2H$
3. R is $CH_3$, Z is $CH_2CO_2H$
4. R is Ph, Z is H
5. R is Ph, Z is $CO_2H$
6. R is Ph, Z is $CH_2CO_2H$
1. (7-Nitro-2-oxo-1,2,3,4-tetrahydro-quinoxalin-5-ylmethyl)-carbamic acid methyl ester
2. 8-(Methoxycarbonylamino-methyl)-6-nitro-3-oxo-1,2,3,4-tetrahydro-quinoxaline-2-carboxylic acid
3. [8-(Methoxycarbonylamino-methyl)-6-nitro-3-oxo-1,2,3,4-tetrahydro-quinoxalin-2-yl]-acetic acid
4. (7-Nitro-2-oxo-1,2,3,4-tetrahydro-quinoxalin-5-ylmethyl)-carbamic acid phenyl ester
5. 6-Nitro-3-oxo-8-(phenoxycarbonylamino-methyl)-1,2,3,4-tetrahydro-quinoxaline-2-carboxylic acid
6. [6-Nitro-3-oxo-8-(phenoxycarbonylamino-methyl)-1,2,3,4-tetrahydro-quinoxalin-2-yl]-acetic acid

UREA OR THIOUREA DERIVATIVES

R is urea or thiourea of formula

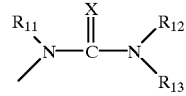

wherein X is O or S;
$R_{11}$ is hydrogen, alkyl, cycloalkyl, heterocycloalkyl, aralkyl, heteroaralkyl, aryl, heteroaryl, hydroxyl, hydroxyalkyl, alkoxyalkyl;
$R_{12}$ is hydrogen, alkyl, cycloalkyl, heterocycloalkyl, aralkyl, heteroaralkyl, aryl, heteroaryl, hydroxyl, alkoxyl, hydroxyalkyl, alkoxyalkyl, alkenyl, alkynyl, alkenylalkyl, alkynylalkyl, $—SO_2R_{14}$, $—SO_2NR_{15}R_{16}$, $—(CH_2)_n SO_2R_{14}$, $—(CH_2)_nSO_2NR_{15}R_{16}$, $—(CH_2)_nCO_2R_{17}$, $—(CH_2)_nCONR_{18}R_{19}$, or is a natural or unnatural amino acid ($\alpha$-, $\beta$-, or $\gamma$-) backbone such as $—CH(R_{20})C(O)OR_{17}$ or $—CH(R_{20})C(O)NR_{18}R_{19}$; wherein $R_{14}$ is hydroxy, alkoxy, or $—NR_{15}R_{16}$; $R_{15}$, $R_{16}$, $R_{18}$, and $R_{19}$ are independently selected from hydrogen alkyl, cycloalkyl, heterocycloalkyl, aralkyl, and aryl; $R_{17}$ is hydrogen, alkyl, aralkyl, cycloalkyl, heterocycloalkyl; $R_{20}$ is hydrogen or a side chain of a natural or unnatural amino acid; n is an integer of from 1 to 4;
$R_{13}$ is hydrogen or joined together with $R_{11}$ to form a mono- or bicyclic ring, unsubstituted or substituted by from 1 to 4 substituents, and is

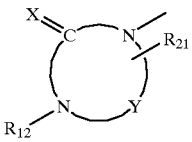

of from 5 to 7 atoms or

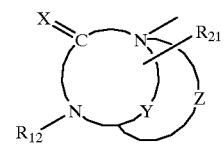

of from 10 to 12 atoms
wherein
Y and Z are each independently carbon which is substituted by hydrogen, halogen, haloalkyl, alkyl, alkoxyl, alkoxyalkyl, $—NR_{15}R_{16}$, aminoalkyl, alkenyl, alkynyl, thioalkyl, alkylthioalkyl, aryl, aralkyl, heteroalkyl, heteroaralkyl, cycloalkyl, $—SO_2R_{14}$, $—SO_2NR_{15}R_{16}$, $(CH_2)_nSO_2NR_{15}R_{16}$, $—(CH_2)_nSO_2R_{14}$, or is $—O—$ or $—S—$;
$R_{21}$ is absent or is hydrogen, alkyl, alkoxy, alkoxyalkyl, $—NR_{13}R_{14}$, aminoalkyl, aralkyl, aryl, heteroaryl, heteroaralkyl, cycloalkyl, heterocycloalkyl, hydroxyl, or hydroxyalkyl, or may represent a gem-dialkyl of two independently selected alkyl groups and when Y is carbon an integral double bond may be optionally located between $C_3$ and $C_4$ of the 5- to 7-membered ring.

Bicyclic structures encompassed in this invention include spiro ring structures, wherein both ends of a second ring are attached to the same carbon unit on the parent ring.

For monocyclic and bicyclic structures wherein Y or Z represent a carbon atom, the structure may also include an integral double bond.

More preferred compounds of Formula I wherein

R is 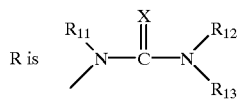

are those wherein
X is O or S;
$R_{11}$ is hydrogen, alkyl, cycloalkyl, aralkyl, heteroaralkyl, hydroxyl, alkoxyl, aralkoxyl;
$R_{12}$ is hydrogen, alkyl, cycloalkyl, heterocycloalkyl, aralkyl, heteroaralkyl, aryl, heteroaryl, $-SO_2R_{14}$, $-SO_2NR_{15}R_{16}$, $-(CH_2)_nSO_2R_{14}$, $-(CH_2)_nSO_2NR_{15}R_{16}$;
$R_{13}$ is hydrogen or joined together with $R_{11}$ to form a monocyclic ring, unsubstituted or substituted by from 1 to 4 substituents and is

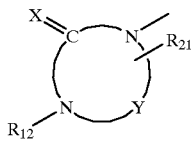

of from 5 to 7 atoms
wherein $R_{21}$ is absent or is hydrogen or alkyl; Y is carbon which is substituted by hydrogen, alkyl, alkoxyl, or aminoalkyl.
Still more preferred are those of Formula I
wherein R is

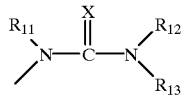

wherein
X is O or S;
$R_{11}$ is hydrogen, alkyl, cycloalkyl, aralkyl, heteroaralkyl, hydroxyl, alkoxyl;
$R_{12}$ is hydrogen, alkyl, cycloalkyl, cycloalkylalkyl, heterocycloalkyl, aralkyl, heteroaralkyl, $-SO_2R_{14}$, $-SO_2NR_{15}R_{16}$; wherein $R_{14}$ is hydroxyl, alkoxyl, $-NR_{15}R_{16}$, or haloalkyl and $R_{15}$ and $R_{16}$ are independently selected from hydrogen, alkyl, cycloalkyl, heterocycloalkyl, aralkyl, and aryl; and $R_{13}$ is hydrogen.
Thiourea derivatives are the corresponding sulfur-containing compounds.
Especially preferred are:

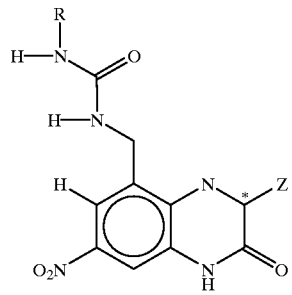

1. R is $CH_3$, z is H
2. R is $CH_3$, z is $CH_2CO_2H$
3. R is $CH_3$, z is $CO_2H$
4. R=Ph, z is H
5. R=Ph, z is $CH_2CO_2H$
6. R=Ph, z is $CO_2H$
7. R=Ph, z is $CH_2OH$ 1. 1-Methyl-3-(7-nitro-2-oxo-1,2,3,4-tetrahydro-quinoxalin-5-ylmethyl)-urea
2. {8-[(3-Methyl-ureido)-methyl]-6-nitro-3-oxo-1,2,3,4-tetrahydro-quinoxalin-2-yl}-acetic acid
3. 8-[(3-Methyl-ureido)-methyl]-6-nitro-3-oxo-1,2,3,4-tetrahydro-quinoxaline-2-carboxylic acid
4. 1-(7-Nitro-2-oxo-1,2,3,4-tetrahydro-quinoxalin-5-ylmethyl)-3-phenyl-urea
5. {6-Nitro-3-oxo-8-[(3-phenyl-ureido)-methyl]-1,2,3,4-tetrahydro-quinoxalin-2-yl}-acetic acid
6. 6-Nitro-3-oxo-8-[(3-phenyl-ureido)-methyl]-1,2,3,4-tetrahydro-quinoxaline-2-carboxylic acid
7. 1-(3-Hydroxymethyl-7-nitro-2-oxo-1,2,3,4-tetrahydro-quinoxalin-5-ylmethyl)-3-phenyl-urea

SULFONAMIDE DERIVATIVES

The sulfonamides include compounds such as

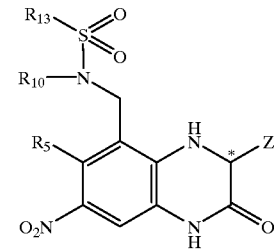

wherein * is R, S, or RS(±);

$R_5$ is hydrogen, alkyl, alkenyl, cycloalkyl, halogen, haloalkyl, aryl, aralkyl, heteroaryl, heteroaralkyl, nitro, cyano, $SO_2CF_3$, $(CH_2)_mCO_2R_9$, $(CH_2)_mCONR_9R_{10}$, $SONR_9R_{10}$, or $NHCOR_9$;

$R_{10}$ is hydrogen or $CH_3$;

Z is $CH_3$, $CH_2OH$, $CO_2H$, $-CH_2CO_2H$, $-CH_2SH$, $CH_2Ph$, or

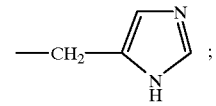

and $R_{13}$ is $CH_3$, phenyl, p-Me-phenyl, p-Cl-phenyl, p-OMe-phenyl, and p-$CO_2R$—Ph wherein R is alkyl.

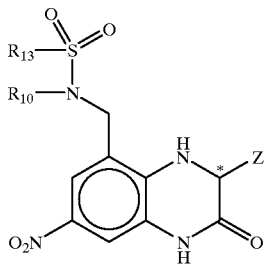

1. $R_{13}$ is $CH_3$, $R_{10}$ is H, Z is H
2. $R_{13}$ is $CH_3$, $R_{10}$ is $CH_3$, Z is H
3. $R_{13}$ is $CH_3$, $R_{10}$ is H, Z is $CH_2OH$
4. $R_{13}$ is $CH_3$, $R_{10}$ is H, Z is

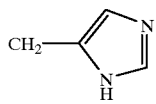

5. $R_{13}$ is $CH_3$, $R_{10}$ is H, Z is $CH_2CO_2H$
6. $R_{13}$ is $CH_3$, $R_{10}$ is H, Z is $CO_2H$
7. $R_{13}$ is Ph, $R_{10}$ is $CH_3$, Z is H
8. $R_{13}$ is Ph, $R_{10}$ is H, Z is H
9. $R_{13}$ is Ph, $R_{10}$ is H, Z is $CH_2OH$
10. $R_{13}$ is Ph, $R_{10}$ is H, Z is

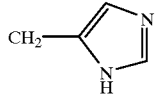

11. $R_{13}$ is Ph, $R_{10}$ is H, Z is $CH_2CO_2H$
12. $R_{13}$ is Ph, $R_{10}$ is H, Z is $CO_2H$

\* R or S (in all cases)

1. N-(7-Nitro-2-oxo-1,2,3,4-tetrahydro-quinoxalin-5-ylmethyl)-methanesulfonamide
2. N-Methyl-N-(7-nitro-2-oxo-1,2,3,4-tetrahydro-quinoxalin-5-ylmethyl)-methanesulfonamide
3. N-(3-Hydroxymethyl-7-nitro-2-oxo-1,2,3,4-tetrahydro-quinoxalin-5-ylmethyl)-methanesulfonamide
4. N-[3-(3H-Imidazol-4-ylmethyl)-7-nitro-2-oxo-1,2,3,4-tetrahydro-quinoxalin-5-ylmethyl]-methanesulfonamide
5. [8-(Methanesulfonylamino-methyl)-6-nitro-3-oxo-1,2,3,4-tetrahydro-quinoxalin-2-yl]-acetic acid
6. 8-(Methanesulfonylamino-methyl)-6-nitro-3-oxo-1,2,3,4-tetrahydro-quinoxaline-2-carboxylic acid
7. N-Methyl-N-(7-nitro-2-oxo-1,2,3,4-tetrahydro-quinoxalin-5-ylmethyl)-benzenesulfonamide
8. N-(7-Nitro-2-oxo-1,2,3,4-tetrahydro-quinoxalin-5-ylmethyl)-benzenesulfonamide
9. N-(3-Hydroxymethyl-7-nitro-2-oxo-1,2,3,4-tetrahydro-quinoxalin-5-ylmethyl)-benzenesulfonamide
10. N-[3-(3H-Imidazol-4-ylmethyl)-7-nitro-2-oxo-1,2,3,4-tetrahydro-quinoxalin-5-ylmethyl]-benzenesulfonamide
11. [8-(Benzenesulfonylamino-methyl)-6-nitro-3-oxo-1,2,3,4-tetrahydro-quinoxalin-2-yl]-acetic acid
12. 8-(Benzenesulfonylamino-methyl)-6-nitro-3-oxo-1,2,3,4-tetrahydro-quinoxaline-2-carboxylic acid The compounds of Formula I are capable of forming pharmaceutically acceptable acid addition salts.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science,* 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as a mixture of cis and trans isomers or R- and S-isomers, or as the individual cis and trans isomers or R- and S-isomers. The mixture of isomers as well as the individual isomers are intended to be encompassed within the scope of the present invention.

In the compounds of the invention, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "carboxyalkyl" means alkyl as above and attached to a carboxy group.

The term "phosphoroalkyl" means alkyl as above and attached to a phosphoro group.

The term "phosphonoalkyl" means alkyl as above and attached to a phosphoro group.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

The term "alkynyl" means a straight or branched chain alkynyl group of 2 to 6 carbon atoms, for example, but not limited to ethynyl, 2,3-propynyl, 2,3- or 3,4-butylnyl.

"Alkoxy" is O-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "aralkyl" means aryl and alkyl as defined above and includes but is not limited to benzyl, 2-phenylethyl, 3-phenylpropyl; a preferred group is benzyl.

The term "heteroaryl" means a heteroaromatic radical which is 2-, 3-, or 4-pyridinyl, 2-, 4-, or 5-pyrimidinyl, or 2-, or 3-thienyl.

"Halogen" is fluorine, chlorine, bromine, or iodine.

The term "haloalkyl" is halogen and alkyl as defined above such as, but not limited to, trifluoromethyl and trichloromethyl.

"Alkylaryl" means aryl as defined above and alkyl as defined above, for example, but not limited to benzyl, 2-phenylethyl, 3-phenylpropyl; a preferred group is benzyl.

The term "heterocycloalkyl" means an alicyclic ring with one or more atoms substituted by a heteroatom, i.e., N, O, and S.

Spiro rings include but are not limited to 5- or 6-membered rings replaced by a heteroatom selected from N, O, and S.

The second ring may also be a gemdialkyl group instead of a ring.

The compounds of the invention exhibit valuable biological properties because of their strong excitatory amino acid (EAA) antagonizing properties at one of several binding sites on glutamate receptors: the AMPA ((RS)-amino-3-hydroxy-5-methyl-4-isoxazolepropionic acid (or kainic acid) binding site on AMPA (non-NMDA) receptors) or the glycine site of NMDA receptors.

The compounds of the present invention exhibit binding affinity for the AMPA receptors as described by Honore T., et al., *Neuroscience Letters,* 1985;54:27–32. Preferred compounds demonstrate $IC_{50}$ values <100 μM in this assay. The compounds of the present invention exhibit binding affinity for the kainate site (non-NMDA receptor) as described by London E. D. and Coyle J., *Mol. Pharmacol.,* 1979;15:492. The compounds of the present invention exhibit binding affinity for the glycine site of the NMDA receptor as described by Jones S. M., et al., *Pharmacol. Methods,* 1989;21:161. To measure functional AMPA antagonist activity, the effects of the agent on AMPA-induced neuronal damage in primary cortical neuronal cultures was examined using techniques similar to those outlined by Koh J. -Y., et al., *J. Neurosci.,* 1990;10:693. In addition, the neuronal damage produced by long-term exposure to 100 μM AMPA may be measured by the release of the cytosolic enzyme lactate dehydrogenase (LDH).

Selected compounds of the present invention are tested by one or more of the above-described assays. The $IC_{50}$ values are a measure of the concentration (μM) of the test substance which inhibits 50% of an induced release from the tested receptors.

Additionally, a preliminary indicator of in vivo CNS activity related to anticonvulsant activity and potential neuroprotection, is a maximal electroshock (MES) assay in CF-1 strain mice (20–25 g) performed with corneal electrodes by conventional methods as described previously (Krall, et al., *Epilepsia,* 1988;19:409–428). The compounds of this invention are expected to generally demonstrate $ED_{50}$ values of <50 mg/kg.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprises conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, and accordingly suitable representative unit dosage forms.

Solid forms of pharmaceutical compositions for PO administration and injectable solutions are preferred.

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid-dependent anoxia, excitatory amino-acid-dependent ischemia, excitatory amino-acid-dependent Parkinsonism, excitatory amino-acid-dependent convulsions, and excitatory amino-acid-dependent migraine. Suitable dosage ranges are 0.1 to 1000 mg daily, 10 to 50 mg daily, and especially 30 to 100 mg daily, dependent as usual upon the exact mode of administration, form in which administered, the indication toward which the administration is directed, the subject involved, and the body weight of the subject involved, and further, the preference and experience of the physician or veterinarian in charge.

The schemes and examples which follow are intended as an illustration of certain preferred embodiments of the invention, and no limitation of the invention is implied.

Schemes 1, 2, and 3 illustrate the preparation of compounds when $R_4$ is nitro; however, nitration step can be substituted by other electrophiles for aromatic electrophilic substitution.

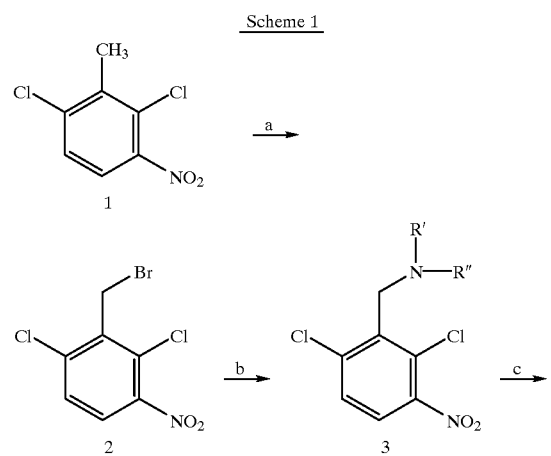

Scheme 1

-continued

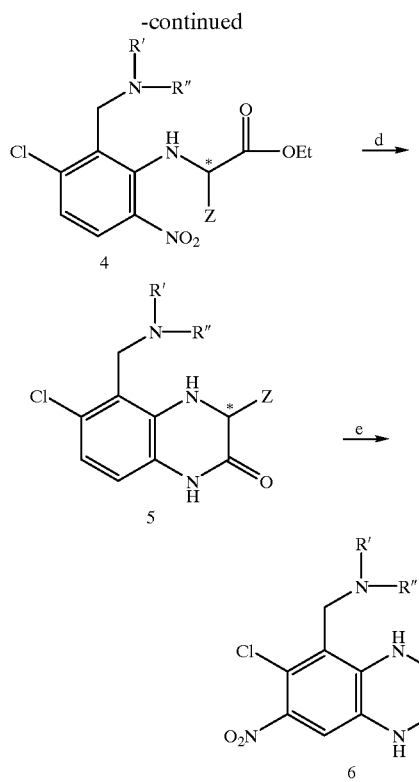

reaction is carried out at temperatures ranging from room temperature to 100° C., preferably 50° C. The product is isolated by aqueous workup followed by purification by column chromatography ($SiO_2$), eluted by mixtures of pet. ether:EtOAc.

Step (d) involves the reductive cyclization of the amino acid intermediate as shown in formula 4 to the corresponding quinoxaline-2-one derivative as shown in formula 5. The reaction is carried out via catalytic reduction of the solution of amino acid derivative as shown in formula 4 in solvents such as THF or methanol, preferably methanol under hydrogen pressure of up to 50 psi in the presence of metal catalysts such as Raney Nickel. Alternatively, the reductive cyclization is carried out in the presence of metal mineral acid mixtures such as Fe/HCl or Zn/HCl.

Step (e) involves nitration of the quinoxaline-2-one derivative as shown in formula 5 to the corresponding 7-nitro derivative as shown in formula 6. The nitration is carried out using nitration mixtures such as $KNO_3/H_2SO_4$, $HNO_3/AcOH$ or $NO_2.BF_4$ in $CH_2Cl_2$ preferably $KNO_3/H_2SO_4$. The product is isolated after aqueous workup.

Scheme 2

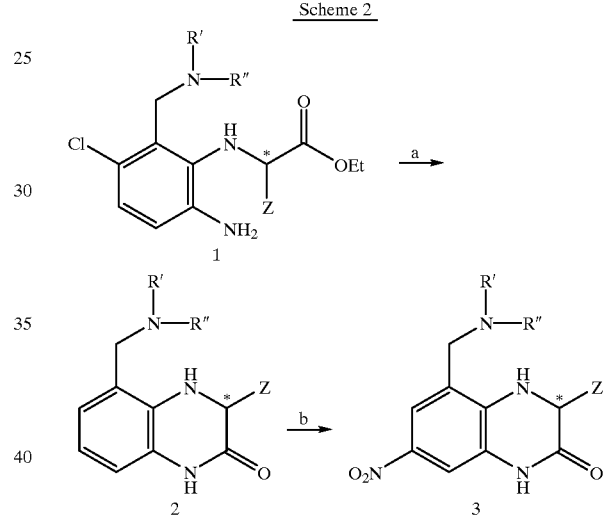

Step (a) involves the side-chain bromination of 2,6-dichloro-3-nitrotoluene as shown in formula 1. The reaction is carried out using brominating agent such as N-bromosuccinimide in the presence of catalytic amounts of radical initiator such as AIBN in a halogenated solvent such as carbon tetrachloride at temperatures ranging from room temperature to reflux, preferably reflux. The product 2,6-dichloro-3-nitrobenzyl bromide as shown in formula 2 is isolated by column chromatography ($SiO_2$), eluted by mixtures of pet ether:EtOAc.

Step (b) involves amination of the benzyl bromide derivative as shown in formula 3 with primary or secondary amines, preferably secondary amines in the presence of base such as the amine itself, or a tertiary amine such as triethylamine, or an inorganic base such as sodium or potassium hydroxide. The reaction is carved out in ethereal solvents such as ether or THF, preferably THF at temperatures ranging from −5° C. to 30° C., preferably 0° C. The product is isolated by normal aqueous workup.

Step (c) involves the coupling of the chloronitrobenzene intermediate as shown in formula 3 with an amino acid derivative to give the amino acid derivative as shown in formula 4. The reaction is carried out in the presence of a base such as tertiary amine base, preferably triethylamine or an inorganic base such as sodium or potassium hydroxide in ethereal solvent such as THF or dioxane or other polar solvents such as methanol or DMF preferably dioxane. The Step (a) involves the catalytic hydrogenation of the amino acid ester intermediate as shown in formula 1 to give the reduced, cyclized and dehalogenated quinoxaline-2-one derivative as shown in formula 2. The catalytic hydrogenation is carried out in the presence of Pd/C (5–20%, preferably 20%) at hydrogen pressure ranging from atmospheric pressure to 50 psi, preferably 50 psi in ethereal solvents such as THF or dioxane, or hydroxylated solvents such as methanol or ethanol preferably methanol.

Step (b) involves nitration of the quinoxaline-2-one derivative as shown in formula 2 to the corresponding 7-nitro-quinoxaline-2-one derivative as shown in formula 3. The nitration is carried out as per the conditions described in Scheme 1, Step (e).

Scheme 3

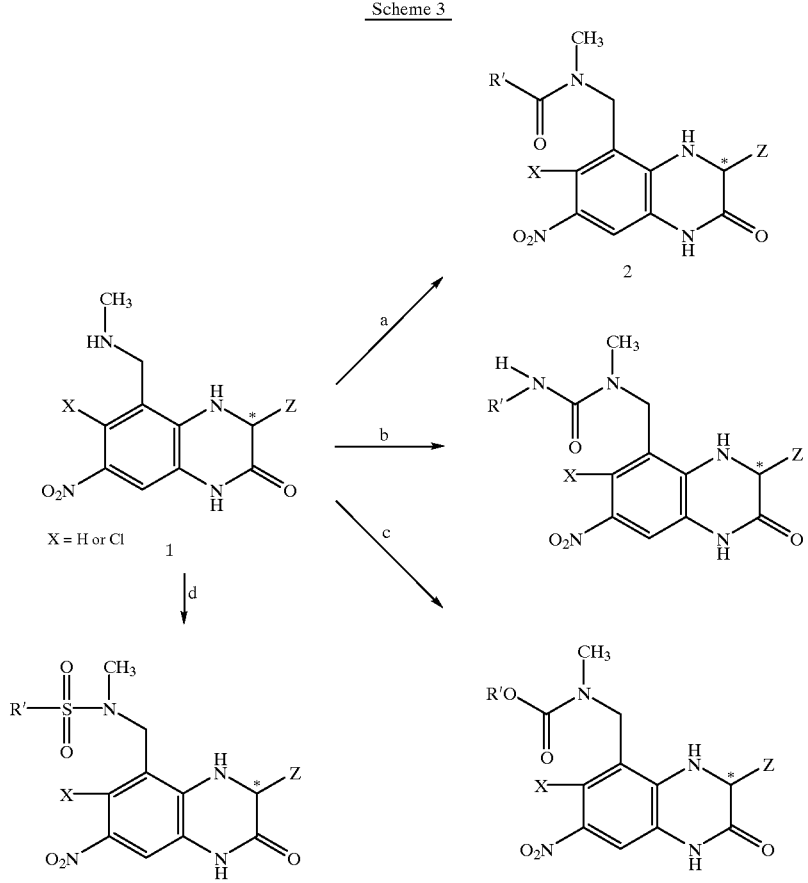

Step (a) involves acylation of the secondary amine functionality in quinoxaline-2-one derivative as shown in formula 1 to give the corresponding amide derivative as shown in formula 2. The acylation is carried out using appropriate acid chlorides in the presence of bases such as trialkylamines, preferably triethylamine or inorganic bases such as sodium or potassium carbonate, or sodium or potassium bicarbonate in ethereal solvents such as dioxane or THF, or polar solvents such as DMF or DMSO, preferably DMF. The product is isolated by aqueous workup.

Step (b) involves reacting the secondary amine functionality in quinoxaline-2-one derivative as shown in formula 1 with isocyanates to give the corresponding urea derivative as shown in formula 2. The reaction is carried out using appropriate isocyanates in the presence of bases such as trialkylamines, preferably triethylamine in ethereal solvents such as dioxane or THF or polar solvents such as DMF or DMSO, preferably DMF at temperatures ranging from 0° C. to 50° C., preferably 20° C. The product is isolated by aqueous workup.

Step (c) involves acylation of the secondary amine functionality in quinoxaline-2-one derivative as shown in formula 1 to give the corresponding carbamate derivative as shown in formula 2. The acylation is carried out using appropriate chloroformate in the presence of bases such as trialkylamines preferably triethylamine or inorganic bases such as sodium or potassium carbonate or sodium or potassium bicarbonate in ethereal solvents such as dioxane or THF or polar solvents such as DMF or DMSO preferably DMF. The product is isolated by aqueous workup.

Step (d) involves sulfonation of the secondary amine functionality in quinoxaline-2-one derivative as shown in formula 1 to give the corresponding amide derivative as shown in formula 2. The sulfonation is carried out using appropriate sulfonyl chlorides in the presence of bases such as trialkylamines, preferably triethylamine or inorganic bases such as sodium or potassium carbonate, or sodium or potassium bicarbonate in ethereal solvents such as dioxane or THF, or polar solvents such as DMF or DMSO, preferably DMF at temperatures ranging from 0° C. to 30° C., preferably 20° C. The product is isolated by aqueous workup.

I claim:

1. A compound of formula

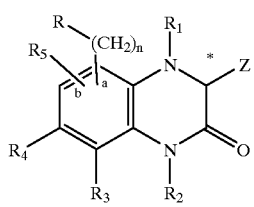

I or a pharmaceutically acceptable salt thereof wherein

* is R, S, or RS(±);

R is a secondary or tertiary amine of the formula

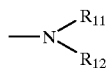

wherein $R_{11}$ and $R_{12}$ are each independently,
hydrogen,
methyl,
ethyl,
propyl,
butyl, or
cyclohexyl;
amino acid deserve of the formula

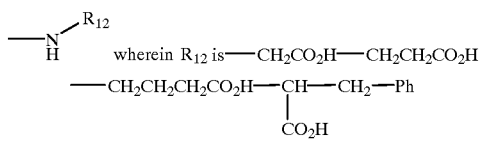

and

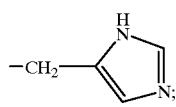

amide of the formula

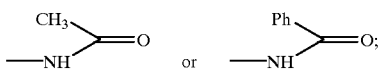

carbamate,

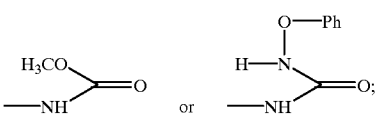

or
urea or a thiourea, of the formula

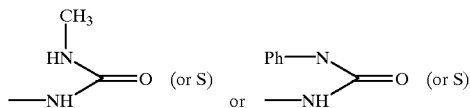

n is an integer of from 1 to 4;
$R_1$ is hydrogen,
  alkyl,
  carboxyalkyl,
  phosphoroalkyl, or
  phosphonoalkyl;
$R_2$ is hydrogen,
  hydroxy, or
  amino;
$R_3$ and $R_4$ are each independently
  hydrogen,
  alkyl,
  cycloalkyl of from 5 to 8 atoms,
  halogen,
  haloalkyl,
  nitro,
  cyano,
  $SO_2CF_3$,
  $C(O)R_6$,
  $(CH_2)_mSO_2R_6$,
  $(CH_2)_mCO_2R_9$ wherein $R_9$ is hydrogen, alkyl, aralkyl, or cycloalkyl,
  $(CH_2)_mCONR_7R_8$,
  $(CH_2)_mSO_2NR_7R_8$, or
  $NHCOR_6$ wherein m is an integer of from 0 to 4, $R_6$ is hydroxy,

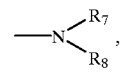

alkyl, haloalkyl, aryl, or aralkyl, and $R_7$ and $R_8$ are each independently hydrogen, alkyl, aralkyl, or aryl;
$R_5$ is hydrogen,
  alkyl,
  alkynyl,
  halogen,
  haloalkyl,
  aryl,
  aralkyl,
  heteroaryl,
  nitro,
  cyano,
  $SO_2CF_3$,
  $C(O)R_6$,
  $(CH_2)_mCO_2R_9$,
  $(CH_2)_mCONR_7R_8$,
  $(CH_2)_mSO_2R_6$,
  $(CH_2)_mSO_2NR_7R_8$ or
  $NHCOR_6$ wherein m, $R_7$, and $R_8$ are as defined above;
Z is the side-chain of an amino acid selected from $—CH_3$, $—CH_2OH$, $—CH_2CO_2H$, $—CH_2SH$ and

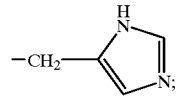

$R_5$ and the $—(CH_2)_n—R$ side chain may be at the a or b position on the ring.

2. A pharmaceutical composition comprising a therapeutically effective amount of a compound according to claim 1 together with a pharmaceutically acceptable carrier in unit dosage form.

3. A method for treating cerebral hypoxia/ischemia which comprises administering a therapeutically effective amount of a compound according to claim 1 to a patient in need of said treatment.

4. A method for treating convulsions which comprises administering a therapeutically effective amount of a compound according to claim 1 to a patient in nned of such treatment.

* * * * *

UNITED STATES PATENT AND TRADEMARK OFFICE
CERTIFICATE OF CORRECTION

PATENT NO. : 6,015,800
DATED : Jan. 18, 2000
INVENTOR(S) : Nikam

It is certified that error appears in the above-indentified patent and that said Letters Patent is hereby corrected as shown below:

Column 31, line 15, "deserve" should read "derivative".

Column 31, line 47 after "alkyl," insert "aralkyl,".

Column 31, line 56 after "alkyl," insert "alkenyl,".

Column 32, line 20 after "alkyl," insert "alkenyl,".

Column 32, line 57, "nned of such" should read "need of said".

Signed and Sealed this

Thirteenth Day of March, 2001

Attest:

NICHOLAS P. GODICI

Attesting Officer

Acting Director of the United States Patent and Trademark Office